US009096556B2

(12) United States Patent
Reddy et al.

(10) Patent No.: US 9,096,556 B2
(45) Date of Patent: Aug. 4, 2015

(54) AMORPHOUS RITONAVIR CO-PRECIPITATED

(75) Inventors: Bandi Parthasaradhi Reddy, Hyderabad (IN); Kura Rathnakar Reddy, Hyderabad (IN); Dasari Muralidhara Reddy, Hyderabad (IN); Bandi Vamsi Krishna, Hyderabad (IN)

(73) Assignee: HETERO RESEARCH FOUNDATION (IN)

( * ) Notice: Subject to any disclaimer, the term of this patent is extended or adjusted under 35 U.S.C. 154(b) by 0 days.

(21) Appl. No.: 14/122,158

(22) PCT Filed: May 21, 2012

(86) PCT No.: PCT/IN2012/000357
§ 371 (c)(1),
(2), (4) Date: Nov. 25, 2013

(87) PCT Pub. No.: WO2012/164575
PCT Pub. Date: Dec. 6, 2012

(65) Prior Publication Data
US 2014/0100252 A1 Apr. 10, 2014

(30) Foreign Application Priority Data
May 27, 2011 (IN) .......................... 1803/CHE/2011

(51) Int. Cl.
*A61K 31/427* (2006.01)
*C07D 417/12* (2006.01)
*C07D 277/28* (2006.01)
*A61K 45/06* (2006.01)
*A61K 47/32* (2006.01)

(52) U.S. Cl.
CPC ............ *C07D 277/28* (2013.01); *A61K 31/427* (2013.01); *A61K 45/06* (2013.01); *A61K 47/32* (2013.01)

(58) Field of Classification Search
CPC .......................... A61K 31/427; C07D 417/12
USPC .................................. 548/146, 204; 514/365
See application file for complete search history.

(56) References Cited

U.S. PATENT DOCUMENTS

| 4,769,236 | A | 9/1988 | Panoz et al. |
|---|---|---|---|
| 5,073,379 | A | 12/1991 | Klimesch et al. |
| 5,484,801 | A | 1/1996 | Al-Razzak et al. |
| 5,541,206 | A | 7/1996 | Kempf et al. |
| 5,559,158 | A | 9/1996 | Al-Razzak et al. |
| 5,610,193 | A | 3/1997 | Al-Razzak et al. |
| 5,635,523 | A | 6/1997 | Kempf et al. |
| 5,648,497 | A | 7/1997 | Kempf et al. |
| 5,674,882 | A | 10/1997 | Kempf et al. |
| 5,914,332 | A | 6/1999 | Sham et al. |
| 5,948,436 | A | 9/1999 | Al-Razzak et al. |
| 6,037,157 | A | 3/2000 | Norbeck et al. |
| 6,232,333 | B1 | 5/2001 | Lipari et al. |
| 6,458,818 | B1 | 10/2002 | Lipari et al. |
| 6,599,528 | B1 | 7/2003 | Rosenberg et al. |
| 6,703,403 | B2 | 3/2004 | Norbeck et al. |
| 6,894,171 | B1 * | 5/2005 | Bauer et al. ................... 548/204 |
| 7,141,593 | B1 | 11/2006 | Alani et al. |
| 7,148,359 | B2 * | 12/2006 | Chemburkar et al. ........ 548/204 |
| 7,183,416 | B2 | 2/2007 | Chemburkar et al. |
| 7,205,413 | B2 * | 4/2007 | Morissette et al. ........... 548/204 |
| 7,364,752 | B1 * | 4/2008 | Fort et al. ...................... 424/455 |
| 7,432,294 | B2 | 10/2008 | Alani et al. |
| 7,981,911 | B2 | 7/2011 | Alani et al. |
| 8,025,899 | B2 | 9/2011 | Berndl et al. |
| 8,268,349 | B2 | 9/2012 | Rosenberg et al. |
| 8,399,015 | B2 | 3/2013 | Rosenberg et al. |
| 8,470,347 | B2 | 6/2013 | Berndl et al. |
| 8,598,216 | B1 * | 12/2013 | Acquasaliente et al. ...... 514/365 |
| 8,691,878 | B2 | 4/2014 | Rosenberg et al. |
| 2004/0014817 | A1 | 1/2004 | Rosenberg et al. |
| 2005/0048112 | A1 | 3/2005 | Breitenbach et al. |
| 2006/0257470 | A1 | 11/2006 | Rosenberg et al. |
| 2007/0249692 | A1 | 10/2007 | Fort et al. |
| 2009/0281132 | A1 | 11/2009 | Velaveni et al. |
| 2010/0021540 | A1 | 1/2010 | Gopinathan et al. |
| 2014/0066468 | A1 | 3/2014 | Parthasaradhi et al. |

FOREIGN PATENT DOCUMENTS

| CA | 2352874 A1 | 6/2000 |
|---|---|---|
| GB | 2053681 A | 2/1981 |
| WO | 9721685 A1 | 6/1997 |
| WO | 9822106 A1 | 5/1998 |
| WO | 0100175 A1 | 1/2001 |
| WO | 0134118 A2 | 5/2001 |
| WO | 0152821 A1 | 7/2001 |
| WO | 2009004653 A2 | 1/2009 |
| WO | 2009153654 A1 | 12/2009 |

OTHER PUBLICATIONS

International Search Report and Written Opinion; International Application No. PCT/IN2012/000357; International Filing Date May 21, 2012; 7 pages.
Dias et al., "Physical and Oral Dog Bioavailability Evaluation of ABT-538: PVP Co-Precipitates", Physical Research Suppl., vol. 13 (9), 1996, pp. S-351 PDD7475.
Law et al., "Physicochemical Considerations in the Preparation of Amorphous Ritonavir-Poly(ethylene glycol) 8000 Solid Dispersions", Journal of Pharmaceutical Sciences, vol. 90, No. 8, Aug. 2001, pp. 1015-1025.
Martin et al., "Method of Preparing an Orally Bioavailable Solid Formulation of an Insoluble Protease Inhibitor as a Coprecipitate with PVP and Other Excipients" Pharmaceutical Research Supply, vol. 13 (9), 1996, pp. S-351 PDD7474.
Reddy et al., U.S. Appl. No. 14/382,075 entitled "Ritanovir Compositions", filed with the USPTO on Aug. 8, 2014.
Reddy et al., U.S. Appl. No. 14/319,755 entitled "Amorphous Form of Lopinavir and Ritonavir Mixture", filed with the USPTO on Jun. 30, 2014.

(Continued)

*Primary Examiner* — Golam M M Shameem
(74) *Attorney, Agent, or Firm* — Cantor Colburn LLP

(57) ABSTRACT

The present invention relates to amorphous ritonavir co-precipitated on copovidone, process for its preparation and pharmaceutical compositions comprising it.

9 Claims, 1 Drawing Sheet

(56) References Cited

OTHER PUBLICATIONS

Zhou et al., "Physical Stability of Amorphous Pharmaceuticals: Importance of Configurational Thermodynamic Quantities and Molecular Mobility", Journal of Pharmaceutical Sciences, vol. 91, No. 8, Aug. 2002, pp. 1863-1872.
Awni W., et al., "Significantly Reduced Food Effect and Pharmacokinetic Variability with a Novel Lopinavir/Ritonavir Tablet Formation," Third IAS Conference on HIV Pathogenesis and Treatment, 2005, Rio de Janeiro, Brazil.
Breitenbach J., et al., "Melt-Extruded Molecular Dispersions," Pharmaceutical Extrusion Technology, 2003, vol. 13, pp. 245-260.
Breitenbach J., et al., "Solid Dispersions by an Integrated Melt Extrusion System," Proceed. Int'l. Symp. Control. Rel. Bioact. Mater., 1998, vol. 25, pp. 804-805.
Breitenbach J., et al., "Two Concepts, One Technology: Controlled-Release Solid Dispersions with Meltrex," Drugs and the Pharmaceutical Sciences, 2003, pp. 125-134.
Chatham S.M., "The Use of Bases in SSM Formulations, " S.T.P. Pharma Pratiques, 1987, vol. 3 (7), pp. 575-582.
Chiou W.L. et al., "Pharmaceutical Applications of Solid Dispersion Systems," Journal of Pharmaceutical Sciences, 1971, vol. 60(9), pp. 1281-1302.
Kaletra Label Oct. 25, 2005.
Kanzer J., et al., "In situ formation of nanoparticles upon dispersion of melt extrudate formulations in aqueous medium assessed by asymmetrical flow field-flow fractionation," Journal of Pharmaceutical and Biomedical Analysis, 2010, pp. 359-365.
Kolter K., et al., "Hot-Melt Extrusion with BASF Pharma Polymers Extrusion Compendium," BASF—The Chemical Company, 2010, pp. 34-35.
Rosenberg J., et al., "Meltrex-Formulations Containing Solid Solutions of Nearly Insoluble Drugs: Formation of Nanoparticles on Dissolution in Water," 28th International Symposium on Controlled Release of Bioactive Materials, 2001, vol. 1, pp. 738-739.
Serajuddin A.T., et al., "Improved Dissolution of a Poorly Water-Soluble Drug from Solid Dispersions in Polyethylene Glycol: Polysorbate 80 Mixtures," Journal of Pharmaceutical Sciences, 1990, vol. 79 (5), pp. 463-464.
Serajuddin A.T.M., "Solid Dispersion of Poorly Water-Soluble Drugs: Early Promises, Subsequent Problems, and Recent Breakthrough," Journal of Pharmaceutical Sciences, 1999, vol. 88(10), pp. 1058-1066.
Serajuddin, A.T.M., "Bioavailability Enhancement of Poorly Water-Soluble Drugs by Solid Dispersion in Surface Active and Self-Emulsifying Vehicles," B.T. Gattefosse, vol. 90, 43-50, 1997.
Sethia S., et al., "Solid Dispersions: Revival with Greater Possibilities and Applications in Oral Drug Delivery," Critical Reviews in Therapeutic Drug Carrier Systems, 2003, vol. 20 (2-3), pp. 215-247.
Sinha S., et al., "Solid Dispersion As an Approach for Bioavailability Enhancement of Poorly Water-Soluble Drug Ritonavir," AAPS PharmSciTech, 2010, vol. 11 (2), pp. 518-527.
Vadnere M.K., "Coprecipitates and Melts" in: Encyclopedia of Pharmaceutical Technology, 2nd Edition, Swarbrick J., eds., Marcel Dekker, Inc, 2002, vol. 1, pp. 641-648.

* cited by examiner

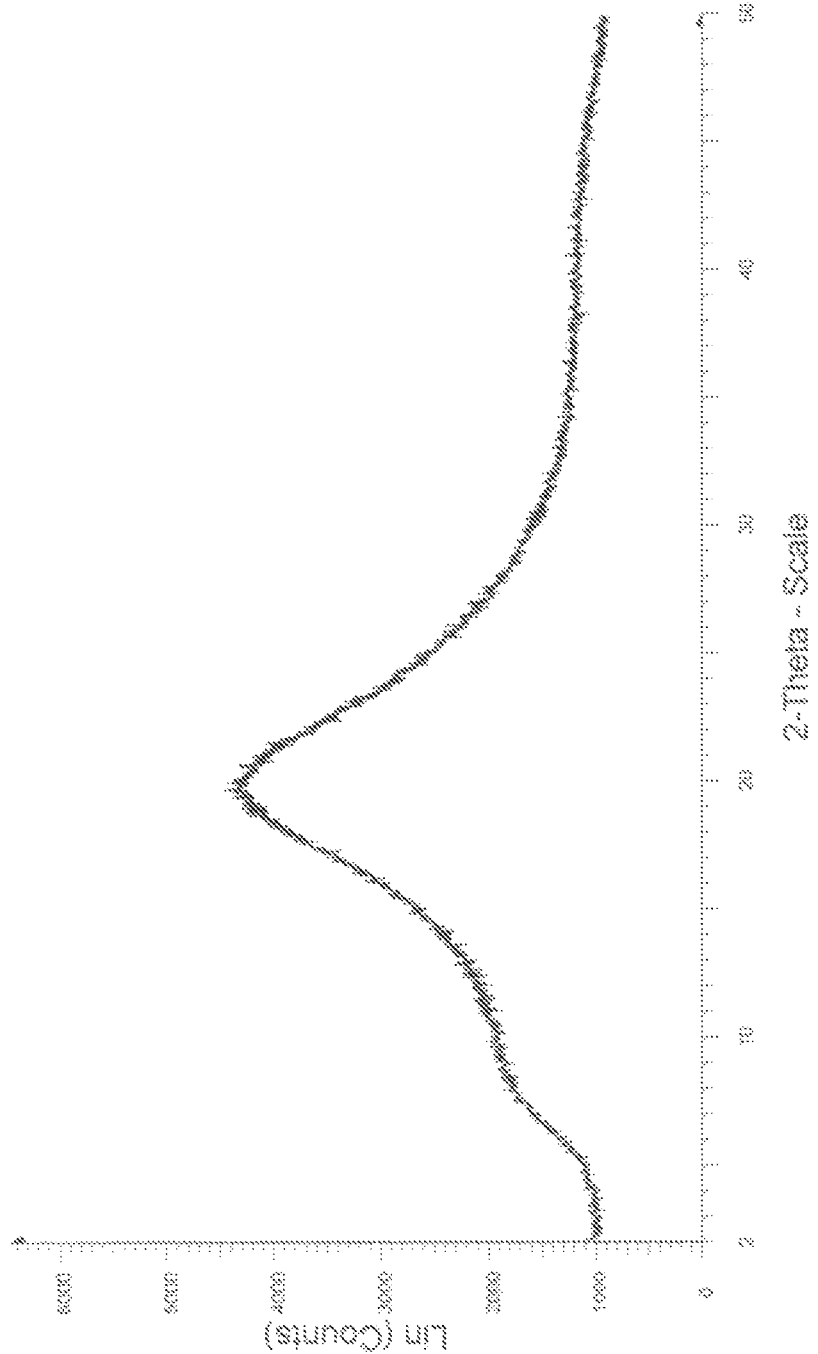

AMORPHOUS RITONAVIR CO-PRECIPITATED

CROSS-REFERENCE TO RELATED

This application is a U.S. national stage of international application No. PCT/IN2012/000357, filed on May 21, 2012, the disclosure of which is incorporated herein by reference in its entirety. Priority is claimed from IN Patent Application No. 1803/CHE/2011, filed on May 27, 2011, the disclosure of which is also incorporated herein by reference in its entirety.

FIELD OF THE INVENTION

The present invention relates to amorphous ritonavir co-precipitated on copovidone, process for its preparation and pharmaceutical compositions comprising it.

BACKGROUND OF THE INVENTION

Inhibitors of human immunodeficiency virus (HIV) protease have been approved for use in the treatment of HIV infection for several years. A particularly effective HIV protease inhibitor was (5S,8S,10S,11S)-10-Hydroxy-2-methyl-5-(1-methylethyl)-1-[2-(1-methylethyl)-4-thiazolyl]-3,6-dioxo-8,11-bis(phenylmethyl)-2,4,7,12-tetraazatridecan-13-oic acid 5-thiazolylmethyl ester, also known as Ritonavir.

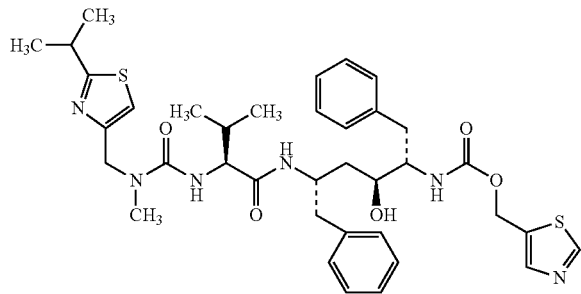 [SMILES: CC(C)c1nc(CN(C)C(=O)N[C@H](C(=O)N[C@@H](Cc2ccccc2)C[C@H](O)[C@H](Cc2ccccc2)NC(=O)OCc2cncs2)C(C)C)cs1]

Ritonavir and its process were disclosed in U.S. Pat. No. 5,541,206.

Polymorphism is defined as "the ability of a substance to exist as two or more crystalline phases that have different arrangement and/or conformations of the molecules in the crystal Lattice. Thus, in the strict sense, polymorphs are different crystalline structures of the same pure substance in which the molecules have different arrangements and/or different configurations of the molecules". Different polymorphs may differ in their physical properties such as melting point, solubility, X-ray diffraction patterns, etc. Although those differences disappear once the compound is dissolved, they can appreciably influence pharmaceutically relevant properties of the solid form, such as handling properties, dissolution rate and stability. Such properties can significantly influence the processing, shelf life, and commercial acceptance of a polymorph. It is therefore important to investigate all solid forms of a drug, including all polymorphic forms, and to determine the stability, dissolution and flow properties of each polymorphic form. Polymorphic forms of a compound can be distinguished in the laboratory by analytical methods such as X-ray diffraction (XRD), Differential Scanning calorimetry (DSC) and Infrared spectrometry (IR).

Solvent medium and mode of crystallization play very important role in obtaining one polymorphic Form over the other.

Ritonavir can exist in different polymorphic Forms, which may differ from each other in terms of stability, physical properties, spectral data and methods of preparation.

Crystalline Form II of ritonavir was disclosed in U.S. Pat. No. 6,894,171. According to the patent also described crystalline form I of ritonavir.

U.S. Pat. No. 7,205,413 disclosed crystalline Form III, Form IV and Form V of ritonavir.

U.S. Pat. No. 7,148,359 disclosed a substantially pure amorphous ritonavir.

Process for the preparation of substantially pure amorphous ritonavir was disclosed in U.S. Pat. No. 7,183,416. According to the patent, substantially pure amorphous ritonavir can be prepared by adding a solution of ritonavir containing methanol or methylene chloride to an anti-solvent such as hexane or methyl t-butyl ether and isolating.

Process for the preparation of amorphous ritonavir was described in *Journal of Pharmaceutical Sciences, Vol. 90, No. 8, P.* 1015-1025 by heating the ritonavir to 135° C. in oil bath, followed by rapid cooling using liquid nitrogen or cold water.

Process for the preparation of amorphous ritonavir was described in *Journal of Pharmaceutical Sciences, Vol. 91, No. 8, P.* 1863-1872 by freeze-drying.

U.S. Pat. No. 5,559,158 disclosed a solid pharmaceutical composition of ritonavir having the composition is encapsulated in a hard gelatin capsule.

U.S. Pat. No. 5,948,436 disclosed pharmaceutical composition comprising a solution of ritonavir having the solution is encapsulated in a hard gelatin capsule or a soft elastic gelatin capsule.

U.S. Pat. No. 7,364,752 disclosed compositions of ritonavir prepared by solid dispersion technique.

Preparation of amorphous Form of ritonavir was described in *Journal of the American association of pharmaceutical scientists, Vol. 13, No. 9, P.* 7473-7476, September 1996 by spray drying of the ritonavir on polyvinylpyrillodone (PVP) and ethanol. Similarly, preparation of amorphous Form of ritonavir was described by layering of the ritonavir on microcrystalline cellulose and silicon dioxide.

It was observed that the amorphous material obtained by the process described in U.S. Pat. No. 7,181,416 was changed into molten state within about 30 minutes. Thus, the amorphous form obtained by the process of U.S. Pat. No. 7,181,416 was shown to be unstable.

We have found a novel amorphous ritonavir co-precipitated on copovidone. The amorphous ritonavir co-precipitated on copovidone is stable, reproducible and so, the amorphous ritonavir co-precipitated on copovidone is suitable for formulating ritonavir. Normally amorphous Forms are hygroscopic. Amorphous ritonavir co-precipitated on copovidone is found to be non-hygroscopic.

Thus, an object of the present invention is to provide amorphous ritonavir co-precipitated on copovidone, process for its preparation and pharmaceutical compositions comprising it.

SUMMARY OF THE INVENTION

In one aspect, the present invention provides amorphous ritonavir co-precipitated on copovidone.

In another aspect, the present invention provides a process for the preparation of amorphous ritonavir co-precipitated on copovidone, which comprises:
  a) dissolving a mixture of ritonavir and copovidone in an alcoholic solvent; and
  b) removing the solvent by drying at about 50 to 80° C. to obtain amorphous ritonavir co-precipitated on copovidone.

Yet in another aspect, the present invention provides a pharmaceutical composition comprising amorphous Form of ritonavir co-precipitated on copovidone and pharmaceutically acceptable excipients.

BRIEF DESCRIPTION OF DRAWINGS

FIG. 1 is an X-ray powder diffraction spectrum of amorphous ritonavir co-precipitated on copovidone.

X-ray powder diffraction spectrum was measured on a bruker axs D8 advance X-ray powder diffractometer having a copper-Kα radiation. Approximately 500 mg of sample was gently flattered on a sample holder and scanned from 2 to 50 degrees two-theta, at 0.019 degrees two theta per step and a step time of 1 second. The sample was simply placed on the sample holder. The sample was rotated at 30 rpm at a voltage 40 KV and current 35 mA.

DETAILED DESCRIPTION OF THE INVENTION

The term "room temperature" refers to temperature at about 25 to 35° C.

According to one aspect of the present invention, there is provided amorphous ritonavir co-precipitated on copovidone.

Amorphous ritonavir co-precipitated on copovidone is found to be stable.

The powdered x-ray diffractogram (PXRD) of amorphous ritonavir co-precipitated on copovidone is shown in FIG. 1.

According to another aspect of the present invention, there is provided a process for the preparation of amorphous ritonavir co-precipitated on copovidone, which comprises:
 a) dissolving a mixture of ritonavir and copovidone in an alcoholic solvent; and
 b) removing the solvent by drying at about 50 to 80° C. to obtain amorphous ritonavir co-precipitated on copovidone.

Ritonavir used in step (a) may be any known crystalline or amorphous Forms.

Preferably the copovidone used in step (a) may be copovidone containing with aerosil and span 20.

The alcoholic solvent used in step (a) may preferably be a solvent or mixture of solvents selected from methanol, ethanol, isopropyl alcohol and n-butanol, and more preferably the alcoholic solvent is ethanol.

The dissolution in step (a) may be performed, for example, by heating the mixture of ritonavir and copovidone in the solvent.

Drying in step (b) may preferably be carried out at about 60 to 70° C. under high vacuum.

According to another aspect of the present invention, there is provided a pharmaceutical composition comprising amorphous Form of ritonavir co-precipitated on copovidone and pharmaceutically acceptable excipients, and optionally other therapeutic ingredients. The amorphous Form of ritonavir co-precipitated on copovidone may preferably be formulated into tablets, capsules, suspensions, dispersions, injectables or other pharmaceutical forms.

The invention will now be further described by the following examples, which are illustrative rather than limiting.

EXAMPLES

Example 1

Preparation of Amorphous Ritonavir Co-Precipitated on Copovidone

A mixture of ritonavir crystalline Form I (80 gm) and copovidone containing with aerosil and span 20 was dissolved in ethanol (250 ml) under stirring at room temperature. The solution was then heated to 40 to 45° C. to obtain a clear solution. The resulting solution was subjected to dry under high vacuum at 60° C. for 13 hours to obtain amorphous ritonavir co-precipitated on copovidone.

Example 2

Preparation of Amorphous Ritonavir Co-Precipitated on Copovidone

Example 1 was repeated using ritonavir crystalline Form II instead of ritonavir crystalline Form I to obtain amorphous ritonavir co-precipitated on copovidone.

Example 3

Preparation of Amorphous Ritonavir Co-Precipitated on Copovidone

Example 1 was repeated using methanol solvent instead of ethanol solvent to obtain amorphous ritonavir co-precipitated on copovidone.

We claim:

1. Amorphous ritonavir co-precipitated with copovidone.

2. The amorphous ritonavir co-precipitated with copovidone of claim 1, having a powder X-ray diffractogram as shown in FIG. 1.

3. A process for the preparation of amorphous ritonavir co-precipitated en with copovidone, which comprises:
 dissolving a mixture of ritonavir and copovidone in an alcoholic solvent; and
 removing the solvent by drying at about 50 to 80° C. to obtain amorphous ritonavir co-precipitated with copovidone.

4. The process as claimed in claim 3, wherein the copovidone used in step (a) is copovidone containing with aerosil and span 20.

5. The process as claimed in claim 3, wherein the alcoholic solvent used in step (a) is a solvent or mixture of solvents selected from methanol, ethanol, isopropyl alcohol and n-butanol.

6. The process as claimed in claim 5, wherein the alcoholic solvent is ethanol.

7. The process as claimed in claim 3, wherein the drying in step (b) is carried out at about 60 to 70° C. under high vacuum.

8. A pharmaceutical composition comprising amorphous Form of ritonavir co-precipitated with copovidone as claimed in claim 1, and pharmaceutically acceptable excipients, and optionally other therapeutic ingredients.

9. The pharmaceutical composition as claimed in claim 8, wherein the amorphous Form of ritonavir co-precipitated with copovidone is formulated into tablets, capsules, suspensions, dispersions or injectables.

* * * * *